(12) United States Patent
Ishii et al.

(10) Patent No.: US 8,748,653 B2
(45) Date of Patent: *Jun. 10, 2014

(54) METHOD FOR PURIFICATION OF OPTICALLY ACTIVE α-FLUOROCARBOXYLIC ACID ESTERS

(75) Inventors: Akihiro Ishii, Saitama (JP); Hideyuki Tsuruta, Fujimino (JP); Yuzuru Morino, Ube (JP); Mikihiro Takahashi, Ube (JP)

(73) Assignee: Central Glass Company, Limited, Ube-shi (JP)

( * ) Notice: Subject to any disclaimer, the term of this patent is extended or adjusted under 35 U.S.C. 154(b) by 0 days.

This patent is subject to a terminal disclaimer.

(21) Appl. No.: 12/673,956

(22) PCT Filed: Aug. 5, 2008

(86) PCT No.: PCT/JP2008/064016
§ 371 (c)(1),
(2), (4) Date: Feb. 17, 2010

(87) PCT Pub. No.: WO2009/025169
PCT Pub. Date: Feb. 26, 2009

(65) Prior Publication Data
US 2011/0021809 A1    Jan. 27, 2011

(30) Foreign Application Priority Data

Aug. 17, 2007  (JP) ................... 2007-212686
Jul. 24, 2008  (JP) ................... 2008-191444

(51) Int. Cl.
C07C 69/63    (2006.01)

(52) U.S. Cl.
USPC ........................................ 560/227

(58) Field of Classification Search
None
See application file for complete search history.

(56) References Cited

U.S. PATENT DOCUMENTS

| | | | |
|---|---|---|---|
| 7,220,878 B2 * | 5/2007 | Kondo et al. | 560/184 |
| 7,462,734 B2 * | 12/2008 | Ishii et al. | 560/111 |
| 7,807,858 B2 * | 10/2010 | Ishii et al. | 570/142 |
| 2006/0167292 A1 | 7/2006 | Gerlach | |
| 2007/0001288 A1 | 1/2007 | Sato | |
| 2008/0071108 A1 * | 3/2008 | Lopez et al. | 560/227 |
| 2008/0125589 A1 | 5/2008 | Ishii et al. | |

FOREIGN PATENT DOCUMENTS

| | | |
|---|---|---|
| EP | 1 780 194 A1 | 2/2007 |
| EP | 1780194 * | 5/2007 |
| JP | 61-271249 A | 12/1986 |
| JP | 2006-83163 A | 3/2006 |
| JP | 2006-169251 A | 6/2006 |
| JP | 2006-290870 A | 10/2006 |
| JP | 2007-13020 A | 1/2007 |
| JP | 2007-212495 | 8/2007 |
| WO | WO 2006/037887 A1 | 4/2006 |
| WO | WO 2006/098444 A1 | 9/2006 |
| WO | WO 2008/090755 A1 | 7/2008 |

OTHER PUBLICATIONS

International Search Report with English translation dated Sep. 9, 2009 (Three (3) pages).
PCT/ISA/237 dated Sep. 9, 2009 (Three (3) pages).
Co-pending U.S. Appl. No. 12/523,440.
Supplementary European Search Report dated Aug. 1, 2013 (six (6) pages).
Elke Fritz-Langhals and Gabi Schultz, Simple Synthesis of Optically Active 2-Fluoropropanoic Acid and Analogs of High Enantiomeric Purity,1993, pp. 293-296, vol. 34, No. 2, Pergermon Press Ltd, Great Britain. (XP-002364902).
Chinese Office Action dated May 16, 2012 (seven (7) pages).

* cited by examiner

*Primary Examiner* — Karl J Puttlitz
(74) *Attorney, Agent, or Firm* — Crowell & Moring LLP

(57) ABSTRACT

Disclosed is a purification method of reducing and removing fluoride ions contained in an optically active α-fluorocarboxylic acid ester represented by formula [1]

[Chemical Formula 30]

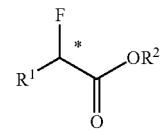

[1]

[in the formula, $R^1$ represents a $C_{1-6}$ alkyl group, $R^2$ represents a $C_{1-4}$ alkyl group, and * represents an asymmetric carbon], the purification method of the optically active α-fluorocarboxylic acid ester being characterized by that a distillation is conducted in the presence of an organic base. By this method, it is possible to greatly reduce the concentration of fluoride ion traces contained in the optically active α-fluorocarboxylic acid ester by a relatively easy operation. Of the organic base, a tertiary amine is preferable, and above all tri-n-butylamine is particularly preferable.

6 Claims, No Drawings

METHOD FOR PURIFICATION OF OPTICALLY ACTIVE α-FLUOROCARBOXYLIC ACID ESTERS

TECHNICAL FIELD

The present invention relates to a method for purifying optically active α-fluorocarboxylic acid esters, which are important intermediates of medicines, agricultural chemicals and optical materials.

BACKGROUND OF THE INVENTION

Optically active α-fluorocarboxylic acid esters, which are the targets in the present invention, are important intermediates of medicines, agricultural chemicals and optical materials. As typical publicly known techniques relating to the present invention, it is possible to cite Patent Publication 1 and Patent Publication 2. These publicly known techniques are methods in which a reaction-terminated liquid of a dehydroxyfluorination is poured into an inorganic base aqueous solution to fix fluoride ions in the aqueous layer to reduce and remove them.

Furthermore, prior to the present application, the present applicant has found that it is possible to easily produce an optically active α-fluorocarboxylic acid ester, in which fluoride ions have reduced, with high chemical purity and optical purity by reacting an optically active α-hydroxycarboxylic acid ester with sulfuryl fluoride ($SO_2F_2$), trifluoromethanesulfonyl fluoride ($CF_3SO_2F$) or nonafluorobutanesulfonyl fluoride ($C_4F_9SO_2F$) in the presence of an organic base and in the absence of a reaction solvent, then adding an acid to a reaction-terminated liquid containing the target product, an optically active α-fluorocarboxylic acid ester, and then conducting a distillation, and an application was already filed [see Japanese Patent Application No. 2007-212495, Example 2 (the first half part), Example 3 (the first half part), Reference Example 1 and Reference Example 2].

Patent Publication 1: Japanese Patent Application Publication 2006-83163

Patent Publication 2: Japanese Patent Application Publication 2006-290870

SUMMARY OF THE INVENTION

It is an object of the present invention to provide a defluorination method suitable for a large-quantity scale production of optically active α-fluorocarboxylic acid esters, which are important intermediates of medicines, agricultural chemicals and optical materials.

Defluorination methods of Patent Publication 1 and Patent Publication 2 have had a problem that recovery percentage after the defluorination lowers in case that the target product has a high solubility in water. Furthermore, there has been a problem that there is a burden on the waste water treatment in a large-quantity scale defluorination, since the amount of water used for fixing fluoride ions is relatively large.

The defluorination method of Japanese Patent Application 2007-212495 is suitable for a large-quantity scale defluorination since operation is easy, but there has been a problem that the defluorination effect is not sufficient. Although the fluoride ion concentration can be reduced to around 100 ppm as an estimation, it has been difficult to achieve a high-degree reduction to less than 10 ppm.

Thus, there has been a strong demand for a defluorination method suitable for a large-quantity scale production of optically active α-fluorocarboxylic acid esters.

As a result of an eager study for solving the above-mentioned task, the present inventors have found that it is possible to easily and efficiently reduce and remove fluoride ions contained in an optically active α-fluorocarboxylic acid ester by conducting a distillation in the presence of an organic base.

That is, the present invention provides a defluorination method suitable for a large-quantity scale production of optically active α-fluorocarboxylic acid esters.

According to the present invention, there is provided a purification method of reducing and removing fluoride ions contained in an optically active α-fluorocarboxylic acid ester represented by formula [1]

[Chemical Formula 1]

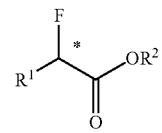

[1]

[in the formula, $R^1$ represents a $C_{1-6}$ alkyl group, $R^2$ represents a $C_{1-4}$ alkyl group, and * represents an asymmetric carbon], the purification method (a first method) of the optically active α-fluorocarboxylic acid ester being characterized by that a distillation is conducted in the presence of an organic base.

The first method may be a second method characterized by that the optically active α-fluorocarboxylic acid ester represented by formula [1], which is subjected to the purification, is one (stereochemistry of the asymmetric carbon is reversed) produced by reacting an optically active α-hydroxycarboxylic acid ester represented by formula [7]

[Chemical Formula 2]

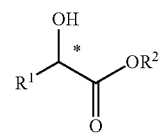

[7]

[in the formula, $R^1$ represents a $C_{1-6}$ alkyl group, $R^2$ represents a $C_{1-4}$ alkyl group, and * represents an asymmetric carbon] with sulfuryl fluoride ($SO_2F_2$), trifluoromethanesulfonyl fluoride ($CF_3SO_2F$) or nonafluorobutanesulfonyl fluoride ($C_4F_9SO_2F$).

The second method may be a third method characterized by that the reaction is conducted in the presence of an organic base and in the absence of a reaction solvent.

Any one method of the first method to the third method may be a fourth method characterized by that the optically active α-fluorocarboxylic acid ester is an optically active 2-fluoropropionic acid ester represented by formula [2]

[Chemical Formula 3]

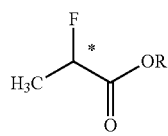

[2]

[in the formula, $R^1$ represents a methyl group or ethyl group, and * represents an asymmetric carbon] and that the organic base made to be present at the time of the distillation is a tertiary amine.

The fourth method may be a fifth method characterized by that the optically active α-fluorocarboxylic acid ester is methyl (R)-2-fluoropropionate represented by formula [3]

[Chemical Formula 4]

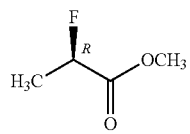

[3]

and that the tertiary amine is tri-n-butylamine.

DETAILED DESCRIPTION

A comparison between characteristics of the present invention and publicly known techniques and the technique described in Japanese Patent Application 2007-212495 not yet published is summarized in the following.

1) The defluorination effect of the present invention is extremely high, and it is possible to highly reduce the fluoride ion concentration to less than 10 ppm. That is an advantageous point as compared with Japanese Patent Application 2007-13020. Furthermore, we have made it clear that the defluorination effect of the present invention is remarkably superior to typical inorganic defluorination agents [a comparison between Example 1 and Reference Example 2 (acid is added to the reaction-terminated liquid, followed by distillation), Comparative Example 2 (sodium fluoride) and Comparative Example 3 (calcium chloride dihydrate)].

2) The defluorination method of the present invention makes it possible to recover even a compound high in solubility in water with good yield. That is an advantageous point as compared with Patent Publication 1 and Patent Publication 2. Methyl (R)-2-fluoropropionate represented by formula [3] is a compound relatively high in solubility in water, but it can be recovered with good yield by applying the defluorination method of the present invention. The compound is preferable as the target compound of the present invention, since it is outstanding in usefulness as an important intermediate of agricultural chemicals.

3) The defluorination method of the present invention is suitable for a large-quantity scale defluorination, since there is almost no burden of the waste water treatment. That is an advantageous point as compared with Patent Publication 1 and Patent Publication 2.

4) In the defluorination method of the present invention, it is exposed to an organic base in the distillation operation under a heated condition, but side reactions, such as racemization of α-position, replacement of the fluorine atom, and the like, which are caused by basicity and nucleophilicity of the organic base, are not found at all. Therefore, it is possible to conduct the defluorination under a condition that high optical purity and chemical purity are maintained.

5) An organic base used in the present invention is advantageous in recovery and reuse too, as compared with inorganic defluorination agents. Recovery and reuse of inorganic defluorination agents are generally difficult, and it is often to discard them after use. On the other hand, recovery and reuse of the organic base can easily be conducted, as mentioned hereinafter.

Thus, it is possible to conduct a defluorination of optically active α-fluorocarboxylic acid ester in large-quantity scale by the present invention.

The purification method of optically active α-fluorocarboxylic acid ester of the present invention is explained in detail.

Firstly, in the present invention, defluorination refers to reduction and removal of fluoride ions contained in an organic compound. Furthermore, the form of existence of fluoride ions contained in an optically active α-fluorocarboxylic acid ester of the present invention is not particularly limited. In general, they exist as "hydrogen fluoride", "a salt or complex formed of an organic base and hydrogen fluoride", "a salt or complex formed of an inorganic base and hydrogen fluoride", or "a complex formed of an optically active α-fluorocarboxylic acid ester and hydrogen fluoride".

As $R^1$ of an optically active α-fluorocarboxylic acid ester represented by formula [1], it is possible to cite methyl group, ethyl group, propyl group, butyl group, amyl group, and hexyl group. The alkyl group having a carbon number of 3 or more can take a straight chain or branch.

As $R^2$ of an optically active α-fluorocarboxylic acid ester represented by formula [1], it is possible to cite methyl group, ethyl group, propyl group, and butyl group. The alkyl group having a carbon number of 3 or more can take a straight chain or branch. It is also possible to form a lactone ring by a covalent bond of the alkyl groups of $R^1$ and $R^2$.

As stereochemistry of the asymmetric carbon of an optically active α-fluorocarboxylic acid ester represented by formula [1], it can take an R configuration or S configuration. Enantiomeric excess (% ee) is not particularly limited. It suffices to use one having 90% ee or greater. Normally, 95% ee or greater is preferable, and particularly 97% ee or greater is more preferable.

The method for producing an optically active α-fluorocarboxylic acid ester represented by formula [1] is not particularly limited. It can be produced with reference to Patent Publication 1, Patent Publication 2, Japanese Patent Application 2007-212495, International Publication 2006/037887 Pamphlet, and Japanese Patent Application Publication 2006-169251 (the production method of unpublished Japanese Patent Application 2007-212495 is described in detail hereinafter). The purification method of the present invention can widely be used for defluorination of the optically active α-fluorocarboxylic acid ester, irrespective of its production method. Particularly, it shows a remarkable defluorination effect on one in which the content of the obtained ester is relatively high. Specifically, it suffices to use one of 70% or greater in weight %. Normally, 80% or greater is preferable, and particularly 90% or greater is more preferable.

The organic base is not particularly limited. As typical ones, it is possible to cite an amine represented by formula [4]

[Chemical Formula 5]

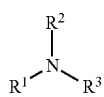

[4]

[in the formula, each of $R^1$, $R^2$ and $R^3$ independently represents a hydrogen atom or $C_{1-12}$ alkyl group (however, $R^1$, $R^2$ and $R^3$ do not take hydrogen atoms at the same time). An alkyl group having a carbon number of 3 or greater can take a straight chain or branch, and a nitrogen-containing hetero ring can also be formed by a covalent bond of the alkyl groups] and a pyridine represented by formula [5]

[Chemical Formula 6]

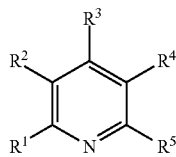

[5]

[in the formula, each of $R^1$, $R^2$, $R^3$, $R^4$ and $R^5$ independently represents a hydrogen atom or $C_{1-6}$ alkyl group. An alkyl group having a carbon number of 3 or greater can take a straight chain or branch.]. Particularly, the former amine is preferable. Of the amine, a tertiary amine is more preferable as compared with a primary amine and a secondary amine. It does not produce, as a side product, even in the distillation operation under a heated condition, an optically active α-fluorocarboxylic acid amide represented by formula [6]

[Chemical Formula 7]

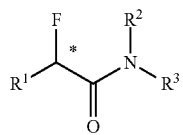

[6]

[In the formula, $R^1$ represents a $C_{1-6}$ alkyl group, and each of $R^2$ and $R^3$ independently represents a hydrogen atom or $C_{1-12}$ alkyl group (however, $R^2$ and $R^3$ do not take hydrogen atoms at the same time). An alkyl group having a carbon number of 3 or greater can take a straight chain or branch, and a nitrogen-containing hetero ring can also be formed by a covalent bond of the alkyl groups of $R^2$ and $R^3$. * represents an asymmetric carbon]. As such tertiary amine, it is possible to cite trimethylamine, triethylamine, diisopropylethylamine, tri-n-propylamine, tri-n-butylamine, tri-n-pentylamine, tri-n-hexylamine, and the like. Furthermore, in the distillation operation, it suffices to use one having a boiling point different from that of an optically active α-fluorocarboxylic acid ester, which is the target compound, by 30° C. or higher under atmospheric pressure. Normally, 40° C. or higher is preferable, and particularly 50° C. or higher is more preferable. Furthermore, it is important to select a tertiary amine that a salt or complex with hydrogen fluoride has a suitable fluidity to easily conduct recovery and reuse. In defluorination of methyl (R)-2-fluoropropionate, which is a preferable target compound of the present invention, tri-n-butylamine is extremely preferable in tertiary amines.

The amount of use of the organic base is not particularly limited. It suffices to use 0.7-100 mols, normally 0.8-75 mols is preferable, and particularly 0.9-50 mols is more preferable, relative to 1 mol of fluoride ions contained in the optically active α-fluorocarboxylic acid ester represented by formula [1]. Depending on the method for producing the optically active α-fluorocarboxylic acid ester represented by formula [1], there are some cases in which it already contains an organic base in a predetermined amount or more. In such cases, it is possible to conduct the distillation purification without newly adding an organic base.

In the purification method of the present invention, it is possible to recover and reuse an organic base used in the defluorination operation. If the distillation is conducted under a preferable operation condition, it is possible to recover the organic base after use in the form of a salt or complex with hydrogen fluoride (a mixture with hydrogen fluoride) from the tank residue (distillation residue). It is possible to recover the organic base with high chemical purity and good yield by neutralizing the tank residue with an alkaline aqueous solution prepared from sodium hydroxide, potassium hydroxide, calcium hydroxide or the like, dividing the separated organic base, conducting according to need a washing with water or dehydration operation, and conducting a distillation. The recovered organic base can be reused without lowering of the defluorination effect. In the case of conducting recovery and reuse in such method, an organic base that is high in fat-solubility and easy in dehydration is preferable. Of course, the method of recovery and reuse is not limited to the above-mentioned method.

As to the operational condition of the distillation, in view of boiling point of an optically active α-fluorocarboxylic acid ester represented by formula [1], which is the target compound, a person skilled in the art can suitably set pressure and bath temperature (still temperature). Distillation under reduced pressure is preferable, since it can suitably lower the distillation temperature. The degree of reduced pressure (It refers to absolute pressure in the system at the time of the distillation. It is the same in the following.) is not particularly limited. It may be conducted in a range of less than atmospheric pressure. Normally, 70 kPa or less is preferable, and particularly 50 kPa or less is more preferable. If it is, however, lower than 0.1 kPa, the efficiency of defluorination becomes low, or the separation efficiency from the organic base becomes low. This may actually result in disadvantage in operation. Therefore, it is not preferable. Thus, it is a preferable mode to conduct the distillation, for example, in a range of 0.5 kPa to 50 kPa.

Furthermore, the column top temperature in the distillation depends on the above-mentioned degree of reduced pressure, but the bath temperature is set naturally at a temperature higher than this column top temperature. The bath temperature also depends on the degree of reduced pressure, but this temperature is in a range of 200° C. or lower. Normally, 175° C. or lower is preferable, and particularly 150° C. or lower is more preferable. Although the bath temperature does not have the lower limit value, it is advantageous to conduct the distillation at a bath temperature of 20° C. or higher, more preferably 30° C. or higher, since the distillation tends to become stable. Therefore, a bath temperature of 20 to 175° C. is cited as a preferable temperature, and 30 to 150° C. is more preferable temperature.

It is possible to further highly reduce and remove fluoride ions contained in the optically active α-fluorocarboxylic acid ester by repeating the defluorination operation of the present invention according to need.

In the purification method of the present invention, the distillation by a combination of an optically active 2-fluoropropionic acid ester represented by formula [2] and a tertiary amine is preferable mode, and particularly the distillation by a combination of methyl (R)-2-fluoropropionate and tri-n-butylamine is a more preferable mode, by judging from usefulness of the target compound, availability of the organic base, a remarkable defluorination effect, operability of the distillation, separability in the distillation between the organic base and the target compound, no occurrence of side reactions, and easiness of recovery and reuse of the organic base, and the like.

[Method For Producing an Optically Active α-fluorocarboxylic acid ester]

In the present invention, as a production method (synthesis method) of an optically active α-fluorocarboxylic acid ester represented by formula [1], which is subjected to the above-mentioned purification, it is possible to cite a method of reacting an optically active α-hydroxycarboxylic acid ester represented by formula [7]

[Chemical Formula 8]

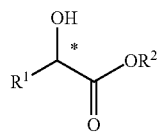

[7]

[in the formula, $R^1$ represents a $C_{1-6}$ alkyl group, $R^2$ represents a $C_{1-4}$ alkyl group, and * represents an asymmetric carbon] with sulfuryl fluoride ($SO_2F_2$), trifluoromethanesulfonyl fluoride ($CF_3SO_2F$) or nonafluorobutanesulfonyl fluoride ($C_4F_9SO_2F$) (stereochemistry of the asymmetric carbon is reversed).

Furthermore, as a method suitable for the production in large-quantity scale, of the above-mentioned, it is possible to cite a method described in Japanese Patent Application 2007-212495. It is very useful as an industrial method, since it has the following two characteristics and the production is possible at high productivity with less waste.

1) That the target reaction proceeds well in a neat condition in which the reaction solvent is never used, and an optically active α-fluorocarboxylic acid ester is obtained with an extremely high optical purity (99% ee or greater in a preferable case) and good yield [Example 2 (the first half part), Example 3 (the first half part), Reference Example 1 and Reference Example 2].

2) That furthermore the reaction-terminated liquid is directly subjected to a distillation purification, thereby making it possible to extremely easily recover an optically active α-fluorocarboxylic acid ester, and at this time an acid is added, and then the distillation purification is conducted, thereby making it possible to effectively reduce the organic base content and the fluoride ion concentration in the optically active α-fluorocarboxylic acid ester to be recovered [a comparison between Reference Example 2 and Example 2 (the first half part), Example 3 (the first half part) and Reference Example 1].

Therefore, a combination (e.g., Example 2 and Example 3) of producing an optically active α-fluorocarboxylic acid ester by a preferable method of Japanese Patent Application 2007-212495 and purifying by a preferable defluorination method of the present invention is an extremely preferable mode.

Since the production method of Japanese Patent Application 2007-212495 is not yet published, it is explained in the following.

The production method contains the following [Production Method 1] to [Production Method 7] and provides an industrial production method of an optically active α-fluorocarboxylic acid ester.

Production Method 1 is a method for producing an optically active α-fluorocarboxylic acid ester represented by formula [1]

[Chemical Formula 10]

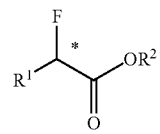

[1]

wherein $R^1$ represents a $C_{1-6}$ alkyl group, $R^2$ represents a $C_{1-4}$ alkyl group, and * represents an asymmetric carbon, the method including reacting an optically active α-hydroxycarboxylic acid ester represented by formula [7]

[Chemical Formula 9]

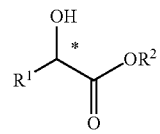

[7]

wherein $R^1$, $R^2$ and * represent the same ones as above, with sulfuryl fluoride ($SO_2F_2$), trifluoromethanesulfonyl fluoride ($CF^3SO^2F$) or nonafluorobutanesulfonyl fluoride ($C_4F_9SO_2F$), in the presence of an organic base and in the absence of a reaction solvent, wherein stereochemistry of the asymmetric carbon in formula [7] is reversed by the reaction.

Production Method 2 is a method for producing an optically active α-fluorocarboxylic acid ester, which is characterized by that an acid is added to a reaction-terminated liquid containing the optically active α-fluorocarboxylic acid ester, which has been obtained by the reaction described in Production Method 1, and then a distillation purification is conducted.

Production Method 3 is a method for producing an optically active α-fluorocarboxylic acid ester according to Production Method 2, which is characterized by that the acid is an organic acid.

Production Method 4 is a method for producing an optically active 2-fluoropropionic acid ester represented by formula [2]

[Chemical Formula 12]

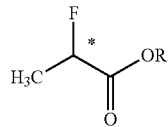

[2]

wherein R represents a methyl group or ethyl group, and * represents an asymmetric carbon, the method including reacting an optically active lactic acid ester represented by formula [8]

[Chemical Formula 11]

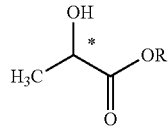

[8]

wherein R and * represent the same ones as above, with sulfuryl fluoride ($SO_2F_2$) or trifluoromethanesulfonyl fluoride ($CF_3SO_2F$), in the presence of triethylamine, diisopropylethylamine, tri-n-propylamine, tri-n-butylamine, tri-n-pentylamine, tri-n-hexylamine, pyridine, 2,3-lutidine, 2,4-lutidine, 2,6-lutidine, 3,4-lutidine, 3,5-lutidine, 2,4,6-collidine or 3,5,6-collidine, and in the absence of a reaction solvent wherein stereochemistry of the asymmetric carbon in formula [8] is reversed by the reaction.

Production Method 5 is a method for producing an optically active 2-fluoropropionic acid ester, which is characterized by that an organic acid is added to a reaction-terminated liquid containing the optically active 2-fluoropropionic acid ester, which has been obtained by the reaction described in Production Method 4, and then a distillation purification under reduced pressure is conducted.

Production Method 6 is a method for producing methyl (R)-2-fluoropropionate represented by formula [3]

[Chemical Formula 14]

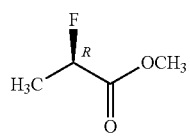

[3]

the method including reacting methyl (S)-lactate represented by formula [9]

[Chemical Formula 13]

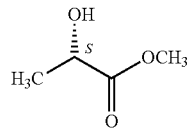

[9]

with sulfuryl fluoride ($SO_2F_2$), in the presence of triethylamine or tri-n-butylamine and in the absence of a reaction solvent.

Production Method 7 is a method for producing methyl (R)-2-fluoropropionate, which is characterized by that benzoic acid is added to a reaction-terminated liquid containing methyl (R)-2-fluoropropionate, which has been obtained by the reaction described in Production Method 6, and then a distillation purification under reduced pressure is conducted.

The best mode for conducting the above [Production Method 1] to [Production Method 7] is shown in detail.

Firstly, there is explained a reaction step for producing an optically active α-fluorocarboxylic acid ester represented by formula [1] by reacting an optically active α-hydroxycarboxylic acid ester represented by formula [7] with sulfuryl fluoride, trifluoromethanesulfonyl fluoride or nonafluorobutanesulfonyl fluoride in the presence of an organic base and in the absence of a reaction solvent.

In the reaction step, the optically active α-hydroxycarboxylic acid ester, which has a stereochemistry reverse to that of the target optically active α-fluorocarboxylic acid ester, is used as the starting raw material, the hydroxyl group is converted to a leaving group (stereoretention), and a bimolecular nucleophilic substitution reaction (stereoinversion) with a fluorine anion is conducted.

As to stereochemistry of the asymmetric carbons of the starting raw material and the target product of the reaction, the step for converting the hydroxyl group to a leaving group proceeds with stereoretention, and the step of conducting a bimolecular nucleophilic substitution reaction with a fluorine anion proceeds with stereoinversion. Therefore, α-position S configuration of an optically active α-fluorocarboxylic acid ester represented by formula [1] is obtained from α-position R configuration of an optically active α-hydroxycarboxylic acid ester represented by formula [7], and similarly α-position R configuration is obtained from α-position S configuration.

As $R^1$ of an optically active α-hydroxycarboxylic acid ester represented by formula [7], it is possible to cite methyl group, ethyl group, propyl group, butyl group, amyl group, and hexyl group, and an alkyl group having a carbon number of 3 or greater can take a straight chain or branch.

In a preferred example, it is possible to recover an optically active α-fluorocarboxylic acid ester represented by formula [1] by directly distilling the reaction-terminated liquid. Upon this, the recovery is easier with a lower boiling point. Therefore, of those, methyl group, ethyl group and propyl group are preferable, and particularly methyl group and ethyl group are more preferable.

As $R^2$ of an optically active α-hydroxycarboxylic acid ester represented by formula [7], it is possible to cite methyl group, ethyl group, propyl group, and butyl group, and an alkyl group having a carbon number of 3 or greater can take a straight chain or branch. Similar to the above, the recovery is easier with a lower boiling point. Therefore, of those, methyl group and ethyl group are preferable, and particularly methyl group is more preferable. Furthermore, It is also possible to form a lactone ring by a covalent bond of the alkyl groups of $R^1$ and $R^2$.

As to stereochemistry of the asymmetric carbon of an optically active α-hydroxycarboxylic acid ester represented by formula [7], it can take R configuration or S configuration. Enantiomeric excess (% ee) is not particularly limited. It suffices to use one having 90% ee or greater. Normally, 95% ee or greater is preferable, and particularly 97% ee or greater is more preferable.

Optically active α-hydroxycarboxylic acid esters represented by formula [7] can similarly be produced from various optically active α-amino acids on the market with reference to Synthetic Communications (US), 1991, Volume 21, Issue 21, p. 2165-2170. Furthermore, a commercial product was used as methyl (S)-lactate used in examples and reference examples.

As a reaction agent for converting the hydroxyl group to a leaving group, it is possible to cite sulfuryl fluoride, trifluoromethanesulfonyl fluoride, or nonafluorobutanesulfonyl fluoride. Of these, in view of atomic economy of fluorine, industrial availability, post-treatment operation and waste treatment, sulfuryl fluoride and trifluoromethanesulfonyl fluoride are preferable, and particularly sulfuryl fluoride is more preferable.

The amount of use of sulfuryl fluoride, trifluoromethanesulfonyl fluoride, or nonafluorobutanesulfonyl fluoride is not particularly limited. It suffices to use 0.7-7 mols, normally 0.8-5 mols is preferable, and particularly 0.9-3 mols is more preferable, relative to 1 mol of an optically active α-hydroxycarboxylic acid ester represented by formula [7].

Although the organic base is not particularly limited, it is possible to cite tertiary amines and pyridines as typical ones. As such organic base, it is possible to cite trimethylamine, triethylamine, diisopropylethylamine, tri-n-propylamine, tri-n-butylamine, tri-n-pentylamine, tri-n-hexylamine, pyridine, 2,3-lutidine, 2,4-lutidine, 2,5-lutidine, 2,6-lutidine, 3,4-lutidine, 3,5-lutidine, 2,3,4-collidine, 2,4,5-collidine, 2,5,6-collidine, 2,4,6-collidine, 3,4,5-collidine, 3,5,6-collidine, and the like. Of these, triethylamine, diisopropylethylamine, tri-n-propylamine, tri-n-butylamine, tri-n-pentylamine, tri-n-hexylamine, pyridine, 2,3-lutidine, 2,4-lutidine, 2,6-lutidine, 3,4-lutidine, 3,5-lutidine, 2,4,6-collidine, and 3,5,6-collidine are preferable. Since the reaction is conducted in the absence of a reaction solvent in the present production method, it is important that a salt or complex of the organic base and hydrogen fluoride or a salt or complex of the organic base and $RfSO_3H$ [in the formula, Rf represents a fluorine atom, trifluoromethyl group, or nonafluorobutyl group], which is produced as a by-product in the reaction system, has an appropriate fluidity so that stirring can be conducted satisfactorily. As such organic base, particularly triethylamine and tri-n-butylamine are more preferable [When the reactions were conducted similar to examples or reference examples by using methyl (S)-lactate (1.0 eq), sulfuryl fluoride (1.2 eq) and an organic base (1.2 eq), and then fluidity of the obtained reaction-terminated liquid at room temperature was examined, fluidity was superior in the case that triethylamine or tri-n-butylamine was used as the organic base to the case that diisopropylethylamine or tri-n-propylamine was used. See Table-1]. Furthermore, in the distillation operation, it suffices to use one having a boiling point different from that of an optically active α-fluorocarboxylic acid ester, which is the target compound, by 30° C. or higher under atmospheric pressure. Normally, 40° C. or higher is preferable, and particularly 50° C. or higher is more preferable. Furthermore, it is important to select an organic base that makes it possible to easily conduct recovery and reuse. In consideration of these viewpoints, tri-n-butylamine is extremely preferable in the production of methyl (R)-2-fluoropropionate, which is a preferable target compound of the present production method.

TABLE 1

| Organic Base | Reaction-terminated Liquid |
|---|---|
| triethylamine | liquid form |
| diisopropylethylamine | sherbet form (solid-liquid condition) |
| tri-n-propylamine | solidified |
| tri-n-butylamine | liquid form |

The amount of use of the organic base is not particularly limited. It suffices to use 0.7-7 mols, normally 0.8-5 mols is preferable, and particularly 0.9-3 mols is more preferable, relative to 1 mol of an optically active α-hydroxycarboxylic acid ester represented by formula [7].

To conduct the reaction in the absence of a reaction solvent, which is an important mode of the present production method, refers to that the reaction is conducted by making a reaction solvent (a liquid such as organic solvent, water, etc.) substantially not to exist in the system, except the above-mentioned reaction reagents. Specifically, it refers to the condition of less than 0.1 L (liter), normally less than 0.07 L is preferable, and particularly less than 0.05 L is more preferable, relative to 1 mol of an optically active α-hydroxycarboxylic acid ester represented by formula [7]. A mode of conducting the reaction without intentionally adding a reaction solvent into the system is a model of conducting the reaction in the absence of a reaction solvent and is extremely preferable. By conducting the reaction in the absence of a reaction solvent, it is possible to produce an optically active α-fluorocarboxylic acid ester represented by formula [1] with high productivity and less waste.

In relation to the reaction temperature, since the reaction is conducted in the absence of a reaction solvent in the present production method, it is important that a salt or complex of the organic base and hydrogen fluoride or a salt or complex of the organic base and $RfSO_3H$ [in the formula, Rf represents a fluorine atom, trifluoromethyl group, or nonafluorobutyl group], which is produced as a by-product in the reaction system, has an appropriate fluidity so that stirring can be conducted satisfactorily. As such reaction temperature, normally −20 to +70° C. is preferable, and particularly −10 to +50° C. is more preferable. Furthermore, it is possible to use a pressure-proof reaction container in the case of conducting the reaction at a reaction temperature that is not lower than boiling point of sulfuryl fluoride, trifluoromethanesulfonyl fluoride, or nonafluorobutanesulfonyl fluoride.

The reaction pressure is not particularly limited. It may be conducted in a range of atmospheric pressure (0.1 MPa) to 2 MPa, normally atmospheric pressure to 1.5 MPa is preferable, and particularly atmospheric pressure to 1 MPa is more preferable. Therefore, it is preferable to conduct the reaction by using a pressure-proof reaction container made of a material such as stainless steel (SUS) or glass (glass lining).

The reaction time is not particularly limited. It may be conducted in a range of not longer than 24 hours. Since it depends on the starting raw material, the organic base, the reaction agent for converting the hydroxyl group to a leaving group, and reaction conditions, etc., it is preferable to monitor the progress condition of the reaction by an analytical means, such as gas chromatography, thin-layer chromatography, liquid chromatography, nuclear magnetic resonance (NMR), etc., and judge the point at which the starting raw material has almost disappeared, as end point.

The optically active α-fluorocarboxylic acid ester obtained by the above-mentioned reaction step can be isolated by subsequently subjecting it to a post-treatment step. As this post-treatment means, there is no particular limitation. In the present production method, however, it is possible to distill the reaction-terminated liquid directly (as it is, without conducting a particular post-treatment operation), since no reaction solvent is used. It is particularly preferable. As mentioned above, in the reaction of the present production method, impurities that are difficult of separation are almost not produced, in spite of being under the condition of the absence of a reaction solvent. Therefore, even if the reaction-terminated liquid is directly subjected to a distillation step, it is possible to recover the target optically active α-fluorocarboxylic acid ester represented by formula [1] with high purity and high optical purity. In the following, this distillation step is explained.

As the condition of distillation, in view of its boiling point, a person skilled in the art can suitably set pressure and bath temperature (still temperature). Distillation under reduced pressure is preferable, since it can suitably lower the distillation temperature. As the degree of reduced pressure (It refers to absolute pressure in the system at the time of distillation. It is the same in the following.) in the case of conducting the distillation under reduced pressure, there is no particular limitation. It may be conducted in a range of less than atmospheric pressure, normally 50 kPa or lower is preferable, and particularly 25 kPa or lower is more preferable. If it is, however, lower than 0.1 kPa, separation efficiency of the distillation becomes low, and it may become disadvantageous in operation. Therefore, it is not preferable. Thus, it is a preferable mode to conduct the distillation, for example, in a range of 0.3 kPa to 25 kPa.

Furthermore, the column top temperature in the distillation depends on the above degree of reduced pressure. The bath temperature is set naturally at a temperature higher than this column top temperature. The bath temperature also depends on the degree of reduced pressure. This temperature is in a range of 200° C. or lower, normally 175° C. or lower is preferable, and particularly 150° C. or lower is more preferable. The bath temperature does not have the lower limit value. If the distillation is conducted at a bath temperature of 20° C. or higher, more preferably 40° C. or higher, the distillation tends to become stable. Therefore, it is advantageous. Thus, a bath temperature of 20 to 175° C. is cited as a preferable temperature, and 40 to 150° C. is a more preferable temperature.

It is possible to obtain the target product with a higher purity by subjecting the recovered distillate to a fractional distillation, according to need.

In the present production method, it is possible to recover and reuse the organic base used in the reaction. If the reaction and the distillation are conducted under preferable operational conditions, it is possible to recover the organic base after use from the tank residue (the distillation residue) in the form of a salt or complex with RfSO$_3$H [in the formula, Rf represents a fluorine atom, trifluoromethyl group or nonafluorobutyl group] (a mixture with RfSO$_3$H) or a salt or complex with hydrogen fluoride (a mixture with hydrogen fluoride) (most of it is in the form of the former). It is possible to recover the organic base with high chemical purity and good yield by neutralizing the tank residue with an alkaline aqueous solution prepared from sodium hydroxide, potassium hydroxide, calcium hydroxide or the like, dividing the separated organic base, conducting according to need a washing with water or dehydration operation, and conducting a distillation. The recovered organic base can be reused without lowering of the reactivity. In the case of conducting recovery and reuse in such method, an organic base that is high in fat-solubility and easy in dehydration is preferable. Of course, the method of recovery and reuse is not limited to the above-mentioned method.

The above distillation step can more preferably be conducted by adding an acid to the reaction-terminated liquid. That is, an acid (preferably an organic acid, more preferably benzoic acid) is added to the reaction-terminated liquid, and then the liquid is subjected to a distillation step, thereby effectively removing the organic base used in the reaction and the remaining fluoride ions (Fluoride ion concentration can be lowered to around 100 ppm. see Reference Example 2). With this, it is possible to produce an optically active α-fluorocarboxylic acid ester represented by formula [1] with higher purity, high productivity and less waste.

In the present production method, a method of obtaining an optically active 2-fluoropropionic acid ester represented by formula [2] by reacting an optically active lactic acid ester represented by formula [8] with sulfuryl fluoride (SO$_2$F$_2$) or trifluoromethanesulfonyl fluoride (CF$_3$SO$_2$F), in the presence of an organic base selected from triethylamine, diisopropylethylamine, tri-n-propylamine, tri-n-butylamine, tri-n-pentylamine, tri-n-hexylamine, pyridine, 2,3-lutidine, 2,4-lutidine, 2,6-lutidine, 3,4-lutidine, 3,5-lutidine, 2,4,6-collidine and 3,5,6-collidine, and in the absence of a reaction solvent is a particularly preferable mode, since usefulness of the product is remarkable, and since the effect of the present production method is remarkable.

Furthermore, a method of obtaining methyl (R)-2-fluoropropionate represented by formula [3] by reacting methyl (S)-lactate represented by formula [9] with sulfuryl fluoride (SO$_2$F$_2$) in the presence of an organic base selected from triethylamine and tri-n-butylamine and in the absence of a reaction solvent is an extremely preferable mode, since usefulness of the product is remarkable, access of the raw material compound is particularly easy, the effect of the present production method is remarkable, etc.

In the above post-treatment step, it is not necessary to specially conduct a distillation by adding an acid to the reaction-terminated liquid to conduct the present application's invention. That is, it is possible to sufficiently achieve the object of the present invention by subjecting an optically active α-fluorocarboxylic acid ester recovered by a distillation without adding an acid to the reaction-terminated liquid, to a distillation by adding an organic base, after the above reaction step. It does not, however, prohibit conducting the above distillation by adding an acid to the reaction-terminated liquid.

EXAMPLES

The form of conducting the present invention is specifically explained by examples, but the present invention is not limited to these examples.

The fluoride ion concentration is expressed in ppm as the weight of fluoride ions relative to the volume of the target compound. For example, one containing 1 mg of fluoride ions in 1 L (liter) of the target compound is referred to as 1 ppm. As specific gravity of methyl (R)-2-fluoropropionate used for calculating the fluoride ion content, 1.07 as the measured value at 20° C. was used.

Furthermore, for the purpose of accurately having a clear picture of the defluorination effect, it is also possible to make an adjustment to the desired fluoride ion concentration by adding a predetermined amount of hydrogen fluoride to methyl (R)-2-fluoropropionate produced by the above-mentioned method.

Example 1

A stainless steel (SUS) distillation apparatus (the number of theoretical plates: 15) was charged with 92.6 kg of methyl (R)-2-fluoropropionate represented by the following formula

[Chemical Formula 15]

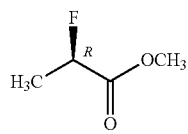

[fluoride ion concentration: 679 ppm (fluoride ion content: 3.1 mol), chemical purity: 99.7%, optical purity: 98.5% ee, and water content: 541 ppm] and 2.3 kg (12.4 mol, 4.0 eq relative to the fluoride ion content) of tri-n-butylamine, followed by a fractional distillation (column top temperature: 45-51° C., and the degree of reduced pressure: 10.7-17.3 kPa), thereby recovering 81.3 kg of a main fraction (Fluoride ions were not detected at all. chemical purity: 100.0%, optical purity: 98.5% ee, and water content: 318 ppm) (recovery percentage: 87.8%).

Comparative Example 1

A stainless steel (SUS) distillation apparatus (the number of theoretical plates: 15) was charged with 91.0 kg of methyl (R)-2-fluoropropionate represented by the following formula

[Chemical Formula 16]

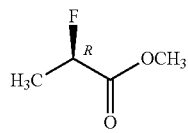

[fluoride ion concentration: 725 ppm, chemical purity: 99.8%, optical purity: 98.5% ee, and water content: 1,427 ppm], followed by a fractional distillation (column top temperature: 50-53° C., and the degree of reduced pressure: 13.3-18.3 kPa), thereby recovering 86.1 kg of a main fraction (Fluoride ion concentration did not lower at all. chemical purity: 99.6%, optical purity: 98.6% ee, and water content: 1,322 ppm) (recovery percentage: 94.6%).

Comparative Example 2 & Comparative Example 3

A reaction container made of polyethylene was charged with 100 g of methyl (R)-2-fluoropropionate represented by the following formula

[Chemical Formula 17]

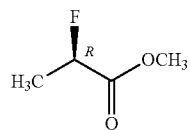

[fluoride ion concentration: 725 ppm, chemical purity: 99.8%, optical purity: 98.5% ee, and water content: 1,427 ppm] and 10 g of an inorganic defluorination agent (sodium fluoride or calcium chloride dihydrate), followed by stirring at room temperature for 15 minutes, filtering the inorganic defluorination agent, and then measuring the fluoride ion concentration. The results have been organized in Table-2. Chemical purity and optical purity did not lower.

TABLE 2

| Comparative Example | Inorganic Defluorination Agent | Fluoride Ion Concentration after Defluorination |
|---|---|---|
| 2 | sodium fluoride | 47 ppm |
| 3 | calcium chloride dihydrate | 37 ppm |

Furthermore, similar defluorination operations were conducted by using alumina or silica gel as an inorganic defluorination agent, but the defluorination effects were inferior to that of Example 1, and it was not possible to lower and remove the fluoride ion concentration to less than 10 ppm.

The findings obtained by Example 1 and Comparative Example 1 to Comparative Example 3 are summarized in the following.

1) The defluorination effect is not found at all by the distillation in the absence of an organic base (a comparison between Example 1 and Comparative Example 1).
2) Typical inorganic defluorination agents are lower in defluorination effect as compared with the distillation in the presence of an organic base (a comparison between Example 1 and Comparative Example 2 and Comparative Example 3).

Example 2

A stainless steel (SUS), pressure-proof, reaction container was charged with 106.8 kg of methyl (S)-lactate represented by the following formula

[Chemical Formula 18]

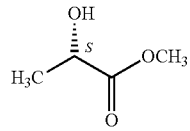

(1.026 kmol, 1.00 eq, optical purity: 99.0% ee) and 190.1 kg (1.026 kmol, 1.00 eq) of tri-n-butylamine, followed by cooling with a circulation-type refrigerant of −10° C. and bubbling from a cylinder 105.1 kg (1.030 kmol, 1.00 eq) of sulfuryl fluoride ($SO_2F_2$). The inside temperature was gradually raised to room temperature, and stirring was conducted at the same temperature for four hours. Conversion of the reaction was found by $^1$H-NMR determination to be 95%.

Then, the reaction-terminated liquid was directly subjected to a distillation under reduced pressure (the degree of reduced pressure; 1.0 kPa, bath temperature; 75° C.). With this, 95.4 kg of a distillate of methyl (R)-2-fluoropropionate represented by the following formula

[Chemical Formula 19]

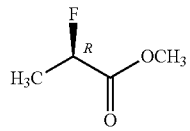

was obtained. Recovery percentage was 84%. Chemical purity (calculated by gas chromatography), optical purity (calculated by chiral gas chromatography), the tri-n-butylamine content (calculated by gas chromatography), the fluoride ion concentration, and the water content of the distillate were respectively 96.5%, 97.4% ee, 1.5%, 543 ppm, and 317 ppm.

$^1$H- and $^{19}$F-NMR spectrums of methyl (R)-2-fluoropropionate were the same as those of Reference Example 1.

560 kg of water was added to the tank residue (distillation residue), followed by cooling with a circulation-type refrigerant of 0° C., adding 48% sodium hydroxide aqueous solution until pH became 12, subjecting the separated organic layer to a two-phase separation, and washing the recovered organic layer with 105 kg of water. Then, a fractional distillation (column top temperature 79-82° C., the degree of reduced pressure 14-16 hPa) was conducted by using a glass-made distillation apparatus (the number of theoretical plates: 15), thereby recovering 156 kg of a main fraction (chemical purity: 99.9% or higher, and water content: less than 0.1%) (recovery percentage 82%). It was possible to reuse the recovered tri-n-butylamine without lowering of reactivity.

A stainless steel (SUS), distillation apparatus (the number of theoretical plates: 15) was charged with 95.4 kg (the fluoride ion content: 2.5 mol) of the above-obtained methyl (R)-2-fluoropropionate and 2.5 kg [13.5 mol, 5.4 eq relative to the fluoride ion content {tri-n-butylamine contained in methyl (R)-2-fluoropropionate was not considered}] of tri-n-butylamine, followed by conducting a fractional distillation (column top temperature 47-52° C., the degree of reduced pressure 11.2-11.7 kPa), thereby recovering 85.1 kg of a main fraction (Fluoride ions were not detected at all. chemical purity 99.9%, optical purity 97.4% ee, and water content 379 ppm) (recovery percentage 89.2%).

Example 3

A stainless steel (SUS), pressure-proof, reaction container was charged with 129.0 kg of methyl (S)-lactate represented by the following formula

[Chemical Formula 20]

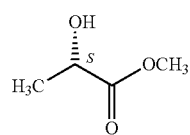

(1.239 kmol, 1.00 eq, optical purity: 99.0% ee) and 275.8 kg (1.488 kmol, 1.20 eq) of tri-n-butylamine, followed by cooling with a circulation-type refrigerant of −10° C. and bubbling from a cylinder 130.4 kg (1.278 kmol, 1.03 eq) of sulfuryl fluoride ($SO_2F_2$). The inside temperature was gradually raised to room temperature, and stirring was conducted at the same temperature for four hours. Conversion and selectivity of the reaction were found by $^1$H-NMR determination to be 99.9% and 94.2%, respectively.

Then, the reaction-terminated liquid was directly subjected to a distillation under reduced pressure (the degree of reduced pressure; 0.4-1.5 kPa, inside temperature; 75-85° C.). With this, 145.1 kg of a distillate of methyl (R)-2-fluoropropionate represented by the following formula

[Chemical Formula 21]

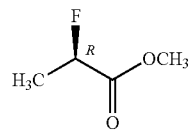

was obtained. Recovery percentage was 94.1% (the total amount was taken out; conversion×selectivity×1/100). Chemical purity (calculated by gas chromatography), optical purity (calculated by chiral gas chromatography), the tri-n-butylamine content (calculated by gas chromatography), and the fluoride ion concentration of the distillate were respectively 87.4%, 97.1% ee, 12.6%, and 28.5 ppm.

$^1$H- and $^{19}$F-NMR spectrums of methyl (R)-2-fluoropropionate were the same as those of Reference Example 1.

A stainless steel (SUS), distillation apparatus (the number of theoretical plates: 15) was charged with 145.1 kg of the above-obtained methyl (R)-2-fluoropropionate (containing 21.3 kg of tri-n-butylamine) (without newly adding tri-n-butylamine), followed by conducting a fractional distillation (column top temperature 49-52° C., the degree of reduced pressure 10.5-12.0 kPa), thereby recovering 113.9 kg of a main fraction (Fluoride ions were not detected at all. chemical purity 99.9%, optical purity 97.2% ee, and water content 275 ppm) (recovery percentage 92.0%).

2577 kg of 2.5% sodium hydroxide aqueous solution was added to the tank residue (the residue of the distillation under reduced pressure) of the reaction-terminated liquid, followed by stirring at an inside temperature of 50-60° C. for three hours, cooling to room temperature, subjecting the separated organic layer to a two-phase separation, and washing the recovered organic layer with 117 kg of water. To 231.7 kg of tri-n-butylamine obtained here, 27.2 kg of the tank residue (containing 21.3 kg of tri-n-butylamine) of the methyl (R)-2-fluoropropionate fractional distillation (defluorination) was added, followed by a fractional distillation (column top temperature 81-84° C., the degree of reduced pressure 1.2-2.0 kPa) by using a stainless steel (SUS), distillation apparatus (the number of theoretical plates: 15) to recover 243.5 kg of a main fraction (chemical purity: 99.9% or higher, and water content: 410 ppm) (recovery percentage 88.3%). It was possible to reuse the recovered tri-n-butylamine without lowering of reactivity.

Reference Example 1

A stainless steel (SUS), pressure proof, reaction container was charged with 12.0 g (115 mmol, 1.00 eq, optical purity 99.0% ee or higher) of methyl (S)-lactate represented by the following formula

[Chemical Formula 22]

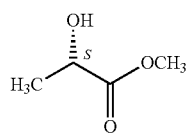

and 13.0 g (128 mmol, 1.11 eq) of triethylamine, followed by cooling in a refrigerant bath of −20° C. and then bubbling from a cylinder 13.5 g (132 mmol, 1.15 eq) of sulfuryl fluoride ($SO_2F_2$). The inside temperature was gradually increased to room temperature, followed by stirring at the same temperature for 2 hours and 30 minutes. Conversion of the reaction was found to be 95% or higher by determination by gas chromatography.

Then, the reaction-terminated liquid was directly subjected to a distillation under reduced pressure (degree of reduced pressure; 15 kPa, bath temperature; 70° C.), thereby obtaining 10.3 g of a distillate of methyl (R)-2-fluoropropionate represented by the following formula.

[Chemical Formula 23]

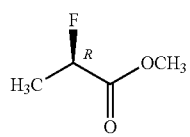

Recovery percentage was 84%. Chemical purity (calculated by gas chromatography), optical purity [calculated by gas chromatography; the ester group is subjected to hydride reduction to convert that to (R)-2-fluoropropanol, and its Mosher acid ester is analyzed], triethylamine content (calculated by $^1$H-NMR), and fluoride ion concentration of the distillate were respectively 94.2%, 99.0% ee or higher, 3.8 mol %, and 342 ppm.

$^1$H- and $^{19}$F-NMR spectrums of methyl (R)-2-fluoropropionate are shown in the following.

$^1$H-NMR [standard substance; $(CH_3)_4Si$, deuterated solvent; $CDCl_3$], δ ppm; 1.59 (dd, 23.6 Hz, 6.8 Hz, 3H), 3.81 (s, 3H), 5.03 (dq, 48.6 Hz, 6.9 Hz, 1H).

$^{19}$F-NMR (standard substance; $C_6F_6$, deuterated solvent; $CDCl_3$), δ ppm; −22.77 (dq, 47.2 Hz, 23.8 Hz, 1F).

Reference Example 2

A stainless steel (SUS), pressure-proof, reaction container was charged with 258 g (2.48 mol, 1.00 eq, optical purity 99.0% ee or higher) of methyl (S)-lactate represented by the following formula

[Chemical Formula 24]

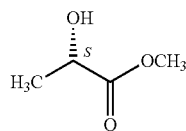

and 278 g (2.75 mol, 1.11 eq) of triethylamine, followed by bubbling from a cylinder 280 g (2.74 mol, 1.10 eq) of sulfuryl fluoride ($SO_2F_2$) while controlling the inside temperature in 0-11° C. The inside temperature was gradually increased to room temperature, followed by stirring at the same temperature for all night. Conversion of the reaction was found to be 92% by determination by gas chromatography.

Then, 76 g (0.62 mol, 2.30 eq relative to triethylamine used excessively) of benzoic acid was added to the reaction-terminated liquid, and it was subjected to a distillation under reduced pressure (degree of reduced pressure; 1.5 kPa, bath temperature; 70° C.), thereby obtaining 193 g of a distillate of methyl (R)-2-fluoropropionate represented by the following formula.

[Chemical Formula 25]

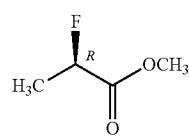

Recovery percentage was 73%. Chemical purity (calculated by gas chromatography), optical purity [calculated by gas chromatography; the ester group is subjected to hydride reduction to convert that to (R)-2-fluoropropanol, and its Mosher acid ester is analyzed], triethylamine content (calculated by $^1$H-NMR), and fluoride ion concentration of the distillate were respectively 97.3%, 99.5% ee, a trace amount (less than 0.2 mol %), and 89 ppm.

$^1$H- and $^{19}$F-NMR spectrums of methyl (R)-2-fluoropropionate were the same as those of Reference Example 1.

In such a manner, it was possible in Reference Example 2 to further greatly reduce triethylamine content and fluoride ion concentration by conducting the distillation after adding an acid to the reaction-terminated liquid, as compared with Reference Example 1.

The invention claimed is:

1. A method for purifying methyl (R)-2-fluoropropionate represented by formula [3]

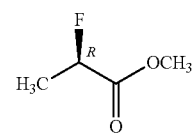

[3]

the method comprising subjecting the methyl (R)-2-fluoropropionate to a distillation in the presence of tri-n-butylamine, thereby removing fluoride ions from the methyl (R)-2-fluoropropionate.

2. A method according to claim 1, wherein the methyl (R)-2-fluoropropionate is produced by reacting methyl (S)-lactate represented by formula [9]

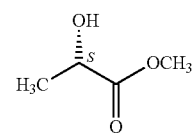

[9]

with sulfuryl fluoride ($SO_2F_2$), trifluoromethanesulfonyl fluoride ($CF_3SO_2F$) or nonafluorobutanesulfonyl fluoride ($C_4F_9SO_2F$).

3. A method according to claim 2, wherein the reaction of claim 2, is conducted in the presence of an organic base and in the absence of a reaction solvent.

4. A method according to claim 1, further comprising recovering the tri-n-butylamine after the distillation and then reusing the tri-n-butylamine in the distillation.

5. A method according to claim 4, wherein recovering the tri-n-butylamine comprises the sequential steps of:
   (a) neutralizing a residue of the distillation with a basic aqueous solution to separate the tri-n-butylamine, and
   (b) distilling the separated tri-n-butylamine.

6. A method according to claim 1, wherein the amount of tri-n-butylamine used is 0.7-100 mols relative to 1 mol of fluoride ions contained in the methyl (R)-2-fluoropropionate.

* * * * *